United States Patent [19]
Jerrett et al.

[11] Patent Number: 6,093,705
[45] Date of Patent: Jul. 25, 2000

[54] METHODS AND COMPOSITIONS FOR SEDATING, ANAESTHETIZING AND EUTHANIZING AQUATIC ORGANISMS

[75] Inventors: Allstair R. Jerrett; Ailsa J. Holland, both of Nelson, New Zealand

[73] Assignee: New Zealand Institute for Crop & Food Research Limited, Canterbury, New Zealand

[21] Appl. No.: 08/913,059

[22] PCT Filed: Mar. 7, 1996

[86] PCT No.: PCT/NZ96/00015

§ 371 Date: Mar. 12, 1999

§ 102(e) Date: Mar. 12, 1999

[87] PCT Pub. No.: WO96/27377

PCT Pub. Date: Sep. 12, 1996

[30] Foreign Application Priority Data

Mar. 7, 1995 [NZ] New Zealand ............................ 270651

[51] Int. Cl.$^7$ ........................ A61K 31/60; A61K 31/045
[52] U.S. Cl. ............................ 514/159; 514/731
[58] Field of Search ..................... 514/159, 731

[56] References Cited

U.S. PATENT DOCUMENTS

| | | | |
|---|---|---|---|
| 4,275,059 | 6/1981 | Flora et al. ........................... | 514/159 |
| 4,404,198 | 9/1983 | Kelley ................................. | 514/159 |
| 4,431,631 | 2/1984 | Clipper ............................... | 424/53 |
| 5,096,709 | 3/1992 | Vandersloot .......................... | 424/195.1 |

FOREIGN PATENT DOCUMENTS

WO 92/18097 of 0000 WIPO.

OTHER PUBLICATIONS

S. Budavari (ed), "The Merck Index", eleventh dedition, published 1989, by Merck & Co., Inc. (Rahway, U.S.A.) pp. 605, 612, 813, 961 and 1207.

J. Reynolds (ed), "Martindale The Extra Pharmocopoeia", thirtieth editions, published 1993, by The Pharmaceutical Press (ILondon) pp. 1031 and 1368.

A. Gennaro (ed), "Remington's Pharmaceutical Sciences", seventeenth edition published 1985, by Mack Pulblishing Company (Easton, Pennsylvania) p. 1306.

Derwent Abstract Accession No. 42127 D/24, BE, 887315 (Colgate Palmolive Co) May 14, 1981.

*Primary Examiner*—Kevin E. Weddington
*Attorney, Agent, or Firm*—Nixon & Vanderhye

[57] ABSTRACT

Methods for sedating, anaesthetising and/or euthanising aquatic organisms, wherein the organism is contacted with methyl salicylate, ethyl salicylate or both, usually in solution. Active compositions for use in such methods are also provided, including compositions containing one or both of methyl salicylate and ethyl salicylate in combination with one or both of eugenol and iso-eugenol.

24 Claims, No Drawings

METHODS AND COMPOSITIONS FOR SEDATING, ANAESTHETIZING AND EUTHANIZING AQUATIC ORGANISMS

FIELD OF THE INVENTION

This invention relates to improved methods for sedating, anaesthetising and/or euthanising aquatic organisms and to compositions for use in such methods.

BACKGROUND OF THE INVENTION

The practice of catching fish or other aquatic organisms usually involves the organisms undergoing some stress. The organisms commonly associate capture with predation and therefore struggle to escape immobilization. This struggle can have a major impact on the post-mortem quality of the tissue of the organism depending upon its duration and at the pre-mortem physical condition of the organism (Lowe, T. E.; Ryder, J. M.; Carragher, J. F.; Wells, R. M. G. 1993: Flesh quality in snapper, *Pagrus auratus*, affected by capture stress. *Journal of Food Science* 58: 770–773; and Jerrett, A. R.; Stevens, J.; Holland, A. J. 1995: Tensile properties of rested and exhausted chinook salmon (*Oncorhynchus tshaivytscha*) white muscle. In press. *Journal of Food Science* (USA)).

In aquaculture, the cultured organisms are usually individually handled during their life cycle. With excitable fish species such as Chinook Salmon (*Oncorhynchus tshawytscha*), great care must be taken to ensure that the animals are not bruised, scaled or in any way disfigured or damaged during handling. A natural, undamaged appearance is often a critical factor in determining the final sale price of the fish.

To achieve optimum product quality during harvesting, the organisms must be maintained in a calm state. One approach which has been investigated is the use of anaesthetics during harvesting. Commonly used anaesthetics such as MS-222, 2-phenoxyethanol, benzocaine and more recently, the sedatives etomidate and metomidate (Kreiberg, H. 1992: Metomidate Sedation Minimises Handling Stress in Chinook Salmon. *Bulletin of the Aquacultural Association of Canada* 92–3: 52–54) have been used to minimise damage during handling but their potential residual toxicity to (or misuse by) humans prevents their use during harvesting.

Non-toxic non-chemical anaesthesia has also been investigated. Commonly used non-toxic alternatives such as cold anaesthesia (Mittal, A. K. and Whitear, M. 1978: A note on cold anaesthesia of poikilotherms. *Journal of Fish Biology*: 519–520) or carbonic acid anaesthesia (Post, G. 1979: Carbonic Acid Anaesthesia for Aquatic Organisms. *The Progressive Fish Culturist* 41(3): 142–144) do induce anaesthesia but can also cause considerable trauma in the process. They are accordingly not appropriate for use in harvesting if the quality of the post-mortem flesh is to be maintained as near pre-mortem as is possible.

It is therefore apparent that a need exists for a readily available food grade anaesthetic having low or no toxicity suitable for use inter alia in the harvesting of aquatic organisms. The ideal chemical anaesthesia for harvesting would be cost-effective, have low or non-irritant qualities and be suitable for use with animals intended for human consumption.

The compounds methyl salicylate and ethyl salicylate have been known for many years. Both are liquids which are slightly soluble in water and miscible in alcohol. They have each been employed in a number of similar commercial applications, including in foods, in perfumery and as counterirritants in both human and veterinary medicine. Further, they are both non-toxic at low concentrations and thus are characterisable as "food grade".

It has now surprisingly been found by the applicants that methyl salicylate and ethyl salicylate are capable of being used as aquatic sedatives, anaesthetics and euthanising agents. It is this finding upon which the present invention is based.

SUMMARY OF THE INVENTION

Accordingly, in a first aspect, this invention provides a method of sedating, anaesthetising or euthanising an aquatic organism comprising the step of contacting said organism with a compound of the formula

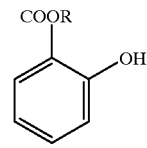

where R is methyl or ethyl.

In a further aspect, the invention provides a method of harvesting an aquatic organism while substantially retaining its pre-mortem flesh quality comprising the step of contacting said organism with a compound of the formula

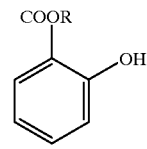

where R is methyl or ethyl.

In yet a further aspect, the invention provides a method of transporting an aquatic organism in a live or pre-rigor state comprising the steps of:

contacting the organism to be transported with a compound of the formula

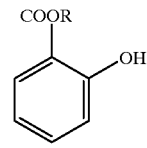

where R is methyl or ethyl in order to induce a sedated, anaesthetised or pre-rigor state in said organism; and
transporting said organism while in said sedated, anaesthetised or pre-rigor state.

In each of the above methods, the compound may be either methyl salicylate or ethyl salicylate, or both.

The active compound(s) (methyl and/or ethyl salicylate) may be in admixture with one or more additional food-grade aquatic sedative, anaesthetic and/or euthanising agents such as eugenol and iso-eugenol.

The compound(s) or the admixture will usually be in solution.

In an additional aspect, the invention provides an active composition suitable for use as an aquatic sedative, anaesthetic or euthanising agent which comprises, in admixture, an effective amount of a compound of the formula

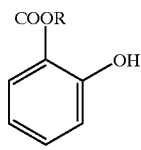

where R is methyl or ethyl, and an effective amount of a solvent or surfactant.

The composition can include one or more additional food-grade aquatic sedative, anaesthetic and/or euthanising agents, with again eugenol and/or iso-eugenol being preferred.

In yet a further aspect, the invention provides an active composition suitable for use as an aquatic sedative, anaesthetic or euthanising agent which comprises, in admixture, an effective amount of at least one compound of the formula

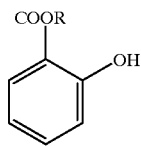

(wherein R is methyl or ethyl)

and an effective amount of at least one compound of the formula

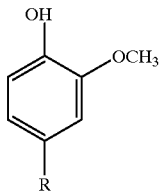

(where R is $CHCHCH_3$ or $CH_2CHCH_2$).

Most conveniently, the composition comprises ethyl salicylate and iso-eugenol.

Optionally, the composition further includes a surfactant.

While the present invention is broadly defined above, it will of course be appreciated by those persons skilled in the art that it is not limited thereto but that it also includes embodiments of which the following description provides examples.

DETAILED DESCRIPTION OF THE INVENTION

As summarised above, the present invention is based upon the applicants' surprising finding that the food grade additives methyl salicylate and ethyl salicylate can be utilised as aquatic sedatives, anaesthetics or euthanising agents. This finding has important consequences for the aquaculture industry, in terms of both the transporting and harvesting of aquatic organisms.

The aquatic organisms to which the methods of the present invention are applied are the so-called primary aquatic organisms which are cold blooded animals living in water and respiring dissolved oxygen. The methods of the present invention are preferably applied to very valuable high grade marketable organisms from an economic point of view. Examples of such organisms include those belonging to the class Pisces such as salmon, trout, char, ayu, carp, crucian carp, goldfish, roach, whitebait, eel, conger eel, sardine, flying fish, sea bass, sea bream, parrot bass, snapper, mackerel, horse mackerel, tuna, bonito, yellowtail, rockfish, fluke, sole, flounder, blowfish, filefish, etc.; those belonging to the class Cephalopoda such as squid, cuttlefish, octopus, etc.; those belonging to the class Pelecypoda such as clam, scallop, ark shell, oyster, etc.; those belonging to the class Gastropoda such as turban shell, abalone, etc.; and those belonging to the class Crustacea such as lobster, prawn, shrimp, crab, squilla, etc.

For use in the present invention, the active compounds methyl salicylate and ethyl salicylate can be readily obtained from commercial sources. Alternatively, methyl salicylate can be obtained by conventional extraction techniques from a variety of natural sources such as the bark of *Betula Lenta L Betulaceae*.

As a still further alternative, methyl salicylate and ethyl salicylate can be prepared by esterification of salicylic acid with methanol or ethanol, respectively.

In the present invention, the active compound (methyl salicylate or ethyl salicylate) can be used in pure form or in a mixture. Such a mixture can be a suspension or emulsion of the active compound(s) in water or can be a mixture in which the active compound(s) are dissolved in an appropriate solvent. Examples of such solvents include alcohols such as ethanol.

It is however preferred that the active compound be used in the form of a composition which includes a surfactant. This surfactant can be any commercially available surfactant having suitable properties, with Polysorbate 80 being preferred.

In addition, methyl salicylate and/or ethyl salicylate can be combined with one or more alternative food-grade aquatic sedative anaesthetic and/or euthanising agents. In particular, a composition which includes one or both of ethyl salicylate and methyl salicylate in combination with one or both of eugenol and iso-eugenol can be formulated. The utility of eugenol and iso-eugenol as aquatic anaesthetics, is described in WO 95/17176.

The amount of active compound employed in the methods of the invention may vary, depending on whether the organism is to be sedated, anaesthetised or euthanised. It will be appreciated that higher concentrations (50 mg/l of active compound or greater) will normally be used where a deep anaesthetic or euthanising effect is desired to be achieved quickly.

However, it will also be understood that a progressive sedative to anaesthetic to euthanising effect can be induced by altering the time the organism is in contact with the active compound(s). Indeed, it is possible for the active compound (s) to be used at concentrations of less than 10 mg/l (eg 8 mg/l), with a progressive sedative, anaesthetic and euthanising effect being induced by increased time exposure to the active solution.

The above concentration of about 8 mg/l of the active compound can be employed when induction of the various graduated effects is not required quickly. It will be appreciated that the use of even lower (down to 3 mg/l or less) or higher concentrations of the active compound(s) (100 mg/l or above) is however not excluded.

The concentration of active agents will of course also vary when methyl and/or ethyl salicylate is combined with other agents such as eugenol and/or iso-eugenol, again depending upon the effect to be induced.

The invention will now be illustrated with reference to the following Examples.

EXAMPLE 1

This example illustrates the graduated effects of methyl salicylate on yellow eyed mullet.

MATERIALS AND METHODS

Experimental Animals

Yellow eyed mullet (*Aldrichetti fosteri*) from the Nelson Harbour had been caught on a sabild rig and kept in the laboratory for two weeks prior to these trials. Animals had been kept in a 700 liters bin with fresh filtered (down to 2 microns) seawater and aeration supplied. Water temperature during this period ranged between 19.7°(C.) and 21.3°(C.).

Animal Sampling and Test Conditions

Animals were dip netted out of the bin and transferred into bins containing 50 liters of fresh seawater. Seven or eight animals were used for each trial. Once animals had been transferred the anaesthetic was mixed in with the water. Alcohol (ethanol) was used as the dispersing agent and the animals were continuously observed for their reactions.

Dosages

Four different dosages of anaesthetic (methyl salicylate in ethanol) were monitored. These dosages were 5 mg/1, 10 mg/1, 15 mg/1 and 20 mg/1 (mg methyl salicylate per liter of seawater) respectively.

Dose-Response Criteria

The responses of the fish to the nominal anaesthetic concentrations were judged against two criteria. The time taken from the addition of the anaesthetic dose to the point where the fish failed to avoid a hand placed in their path gave an empirical estimation of a sedative effect. Animals in this state could be removed from the water but would rouse themselves and slightly struggle if they were not returned to the water within 5 to 10 seconds. Ventilation was often exaggerated and the fish would tend to swim slightly "nose up" near the tank surface. Fish in this stage were characterised as "handleable" for the purposes of this experiment.

The time taken from the addition of the anaesthetic dose to the point where the animals were insensible to forced extension of the operculum and contact with the gill lamellae gave an indication of an anaesthetic effect. In this state the fish exhibited a loss of equilibrium but weak swimming motions were often present. Ventilation was often erratic and exaggerated at this stage. Fish that had not reached this state would respond within 30 seconds of contact with the gill lamellae with a reflexive "cough".

RESULTS AND DISCUSSION

Once the anaesthetic formulation was introduced into the seawater, increasing sedation was characterised by a slight increase in swimming speed, moderate ventilation and a progressive decrease in the distance at which the tank walls and water surface were perceived. At the point of "handleability", the animals were often unaware of the tank walls until contact was made. A loud noise could elicit a transient startle response at this level of sedation.

Progression from the point of "handleability" to the loss of the "coughing" reflex is characterised by a progressive loss of equilibrium and effective swimming motions. The fish were insensitive to loud noises and physical restraint. The erratic ventilation observed at this stage slowed and eventually ceased as anaesthesia deepened leaving the fish inert and apparently unresponsive to physical stimuli.

The results for each dosage are as follows:

5 mg/l

Eight animals were used for this trial.

At 1 minute 50 seconds after introduction of anaesthetic, all animals were rising to the surface and displaying a slightly nose up attitude.

At 2 minutes 12 seconds after introduction of anaesthetic, all animals were sedated. Animals could be easily handled but were still aware of being out of the water with slight initial struggling. Animals that had been caught in the corner of the bin showed some signs of agitation.

At 8 minutes 4 seconds after introduction of anaesthetic, all animals were in a nose up tail down attitude but did not appear to be any closer to an anaesthetised state.

At 37 minutes 33 seconds after introduction of anaesthetic, two animals had lost equilibrium to the extent that though they were still displaying swimming motions their underbelly's were exposed.

At 41 minutes 6 seconds after introduction of anaesthetic, one animal had completely lost equilibrium and was in an anaesthetised state.

At 60 minutes after introduction of anaesthetic, the animals were placed in fresh seawater and recovery was immediate. The one animal that had been anaesthetised assumed an upright position within 2 to 3 seconds.

10mg/l

Eight animals were used for this trial.

At 2 minutes 29 seconds after introduction of anaesthetic, all animals were sedated and easily handleable.

At 6 minutes 42 seconds, one animal was anaesthetised.

At 8 minutes 39 seconds, three animals were anaesthetised.

At 9 minutes 58 seconds, five animals were anaesthetised.

At 11 minutes, all animals were anaesthetised.

At 11 minutes 38 seconds, the animals were placed in fresh water.

At 2 minutes 14 seconds after being placed in fresh water, three animals were upright.

At 2 minutes 43 seconds, four animals were upright.

At 3 minutes 8 seconds, six animals were upright.

At 3 minutes 24 seconds, all animals were upright.

At 11 minutes 32 seconds, all animals started to lighten in colour.

At 12 minutes 37 seconds, all animals were startleable and completely recovered.

15 mg/l

Eight animals were used for this trial.

At 1 minutes 18 seconds after introduction of anaesthetic, all animals were handleable;

at 2 minutes 40 seconds, one animal was anaesthetised;

at 3 minutes 23 seconds, all animals were anaesthetised;

at 5 minutes, all animals were placed in fresh water;

at 1 minute 52 seconds after being placed in fresh water, two animals had recovered; and at 4 minutes 44 seconds, all animals had recovered.

20 mg/l

Seven animals were used for this trial.

At 41 seconds after introduction of anaesthetic, all animals were sedated;

at 2 minutes 56 seconds, one animal was anaesthetised;

at 4 minutes 25 seconds, all animals were anaesthetised;

at 5 minutes 14 seconds, animals were placed in fresh water;

at 3 minutes after being placed in fresh water, one animal was upright; and at 7 minutes 39 seconds, all animals had recovered.

These results are summarised in Table 1.

TABLE 1

Reaction Times (100% of Test Animals)

| Concentration | Time to Sedation | Time to Anaesthesia | Time to Recovery |
| --- | --- | --- | --- |
| 5 mg/l | 2 m 12 s | — | 2 s |
| 10 mg/l | 2 m 29 s | 11 m | 3 m 24 s |
| 15 mg/l | 1 m 18 s | 2 m 23 s | 4 m 44 s |
| 20 mg/l | 41 s | 4 m 25 s | 7 m 39 s |

EXAMPLE 2

This example illustrates in greater detail the effects of both methyl and ethyl salicylate, alone or in combination with other active agents, with different solvents/surfactants and with different species of organisms.

MATERIALS AND METHODS

Chemical Reagents

Technical grade 99% ethyl salicylate, 99% methyl salicylate and 99% iso-eugenol were used in these trials. For each trial the anaesthetic agents being tested were either dispersed in Polysorbate 80 (Liposorb 20™), Polysorbate 20 (Tween 20™), or 99% ethanol to produce a stock 50% (w/w) dispersant\anaesthetic mixture. Immediately prior to each trial, the required quantity of the mixture was weighed then dispersed in approximately 500 ml seawater to form a milky suspension.

Test Conditions

Six 1.5 m$^3$, black cylindrical tanks were used. Each tank was supplied with sand-filtered seawater in a flow-through basis with auxiliary air supplied to ensure dissolved oxygen saturation at the onset of each trial. The salinity was 35 ppt (Atago S/Mill Refractometer, Japan) and water temperature ranged from 18.8 to 20.2° C. during the course of the trials. Prior to the dispersion of the anaesthetic mixture, the water supply was shut off and the tank water level reduced to approximately 1.35 m$^3$. On commencement of each trial the milky suspension was added to the surface of the test tank and dispersed using the bubble stream of the auxiliary aeration for approximately 15 seconds. Once dispersion was complete the auxiliary air was shut off. Dissolved oxygen was maintained above 86% saturation with close to saturation levels being found in the short exposure, high dose trials (YSI Model 57 Dissolved Oxygen Meter, USA).

Subject Animals

All specimens used in these trials were reared in and/or were resident at our laboratory for at least 6 months prior to use in these experiments. The following species were tested during this series of experiments:

Queen Paua (*Haliotis australis*);

Yellow Eye Mullet (*Aldrechettaforsteri*);

Chinook Salmon (*Oncorhynchus tshawytscha*); and

Snapper (*Pagrus auratus*).

All animals were transferred to the experimental tanks at least 24 hours prior to experimentation.

Criteria Used to Stage the Sedative or Anaesthetic Effects

The response of the fish species to the anaesthetic mixtures was divided into four phases. With the exception of the initial criteria used to describe the "calming" action of the mixtures (Phase 1), the time taken from the introduction of the anaesthetic to the time taken for the last fish in each experimental group to show symptoms appropriate to each stage was recorded. With Phase 1, the mean time for all of the trial group to swim in the top 300 mm of the tank was recorded. Loss of equilibrium was not used to stage the progress as this effect was common to several phases of anaesthesia and often interrupted with periods in which equilibrium was regained. The time taken for the last fish in each group to succumb to each phase of anaesthesia was selected as the measured parameter as this may give a more conservative, "worst-case" indication of the treatment effects as they are affected by confounding variables such as animal size, fatigue, stress, water temperature and anaesthetic mixing. These animal condition and handling-related effects are likely to be the cause of the more rapid anaesthesia noted in Example #1. In this example the animals were not tank-acclimated, were handled in a manner that caused immediate struggling and ranged from approximately 30 to 50 grams in body weight.

Phase 1—Surface swimming as a result of an increased tolerance of normally alarming stimuli resulting in subdued panic or escape responses Prior to addition of the anaesthetic mixtures all of the fish showed mild wariness or alarm in response to activity around the tank. This was characterised by the animals remaining close to the bottom of the tank, rapid pectoral and caudal fin movements and darting movements in response to sudden movements by the experimenters. A less excitable state was observed in which the animals consistently swarm in the top 300 mm of the tank irrespective of the presence of humans. This state deepened with time with the animals swimming increasingly on the surface. During this state they could not be touched and were very aware of tank walls or objects within the tank. Sudden movements or noises could only elicit a transitory startle response with a normal resumption of surface swimming occurring within seconds.

Phase 2—Handleable

This phase was characterised by a loss of awareness of surroundings to the extent that the animals could be touched without eliciting an escape response. Any attempt at restraint would elicit an escape response. An object placed within approximately 30 to 40 mm of an animal's head would elicit avoidance behaviour without an escape response. At this phase the animals were able to be guided around the tank surface without physical contact and without eliciting a panic escape response. The external colour of the fish was noticeably darkening during this phase. Ventilation was often exaggerated during this phase.

Phase 3—Sedation

Animals in this phase would not avoid an object placed within their path. They could be removed from the water but would rouse themselves and struggle if not returned to the water within 5 to 15 seconds. Ventilation was often exaggerated and the fish would swim "nose up" near the tank surface. The external colour had typically reached its maximum colour change or darkening by this stage.

Phase 4—Anaesthesia

Animals in this phase had typically lost equilibrium and had often sunk to the tank bottom. Gills were typically slightly flared and ventilation absent. The animals would not respond within 10 seconds to forced distension of the operculum and contact with the gill lamellae.

Recovery

The time taken for recovery was measured from the removal of the animals from the anaesthetic and introduction into fresh seawater till the return to a state equivalent to that found in Phase 1.

RESULTS

As response to anaesthesia can vary considerably with animal stress and fatigue, the observations were grouped into trials that occurred within the same day using the same species and chemicals.

| Dose (mg/l) | Phase 1 (min:sec) | Phase 2 (min:sec) | Phase 3 (min:sec) | Phase 4 (min:sec) | Recovery (min:sec) | Number of fish | Mean fish weight (g) |
|---|---|---|---|---|---|---|---|
| \multicolumn{8}{c}{Trial #1 — Ethyl Salicylate Polysorbate 80 (P80) mixture applied to Yellow Eye Mullet} ||||||||
| 0(80 mg/l P80) | not achieved | not achieved | not achieved | not achieved | unable to measure | 5 | unable to measure |
| 3 | 1'17" | 62'54" | not achieved | not achieved | unable to measure | 5 | unable to measure |
| 50 | 0'54" | — | 2'26" | 9'09" | 8'04" | 5 | 125.5 |
| 100 | 1'17" | — | 2'04" | 5'38" | 8'17" | 5 | 160.2 |
| \multicolumn{8}{c}{Trial #2 — Methyl Salicylate Polysorbate 80 (P80) mixture applied to Yellow Eye Mullet} ||||||||
| 3 | 2'17" | not achieved | not achieved | not achieved | unable to measure | 5 | unable to measure |
| 50 | 1'04" | 1'53" | 8'52" | 16'02" | 7'20" | 5 | 177.0 |
| 100 | 0'46" | 1'08" | 2'01" | 6'49" | 4'06" | 5 | 165.5 |
| \multicolumn{8}{c}{Trial #3 — Ethyl Salicylate Polysorbate 80 (P80) mixture applied to Chinook Salmon} ||||||||
| 20 | 2'48" | 2'55" | 4'10" | 45'52" | 29'11" | 4 | 276.0 |
| \multicolumn{8}{c}{Trial #4 — Ethyl Salicylate\Tween 20 mixture applied to Chinook Salmon} ||||||||
| 20 | 1'34" | 3'58" | 13'46" | not achieved | 23'50" | 6 | 315.9 |
| \multicolumn{8}{c}{Trial #5 — Ethyl Salicylate\Tween 20 mixture applied to Snapper} ||||||||
| 20 | 1'34" | 6'02" |  | 50'46" | 17'54" | 6 | 315.9 |
| \multicolumn{8}{c}{Trial #6 — Ethyl Salicylate\ethanol mixture applied to Snapper} ||||||||
| 20 | 3'44" | — | 36'31" | 91'00" | not measured | 3 | 147.6 |
| \multicolumn{8}{c}{Trial #7 — Ethyl Salicylate\ethanol mixture applied to Yellow Eye Mullet} ||||||||
| 20 | 2'59" | 18'15" | 34'34" | 91'00" | 30'00" | 6 | 120.9 |
| \multicolumn{8}{c}{Trial #8 — Ethyl Salicylate\Polysorbate 80 mixture applied to Snapper} ||||||||
| 40 | 2'14" | 10'11" | 22'11" | 35'42" | 6'12" | 7 | not measured |
| \multicolumn{8}{c}{Trial #9 — Methyl Salicylate\Polysorbate 80 mixture applied to Chinook Salmon} ||||||||
| 40 | 2'55" | 5'44" | 9'47" | not achieved | 14'09" | 3 | 268.6 |
| \multicolumn{8}{c}{Trial #10 — Ethyl Salicylate\Iso-eugenol\Polysorbate 80 (P80) mixture applied to Yellow Eye Mullet} ||||||||
| 8 mg/l iso. 8 mg/l ethyl. 16 mg/l P80 | 1'28" | 3'36" | 5'33" | 50'26" | 7'10" | 5 | 160.7 |
| 50 mg/l ethyl. | 0'38" | ' | 1'24" | 16'28" | 7'21" | 5 | 117.5 |
| 50 mg/l ethyl. 20 mg/l iso. 70 mg/l P80 | 0'34" | — | 1'20" | 2'29" | 14'30" | 5 | 181.1 |
| 20 mg/l iso. 20 mg/l P80 | 0'35" | 2'35" | 4'35" | 15'33" | 36'42" | 5 | 145 |
| \multicolumn{8}{c}{Trial #11 — Ethyl Salicylate\Polysorbate 80 (P80) mixture applied to Queen Paua (Abalone)} ||||||||

| Dose (mg/l) | Time to loss of foot adhesion to tank surface (min:sec) | Recovery of adhesion (min:sec) | Number of abalone | Mean weight (g) |
|---|---|---|---|---|
| 20 | 21'25" | 19'00" | 19 | 81.5 |

DISCUSSION

General Effects

Both methyl salicylate and ethyl salicylate were effective in immobilising the aquatic animals tested. Ethyl salicylate produced yellow eye mullet that were handleable (Phase 2) at a concentration of 3 mg/l while methyl salicylate could only produce a surface swimming response (Phase 1) at this concentration. At the higher concentrations of 50 and 100 mg/l ethyl salicylate produced a deeper anaesthesia more rapidly than methyl salicylate (Trials #1 and 2). This conclusion is supported by the slightly more rapid recovery shown by mullet treated with the methyl salicylate Polysorbate 80 formulation (Trials #1 and 2). Both methyl and ethyl salicylate produced muscle twitches or spasms in Phase 4 chinook salmon and mullet although this effect was much reduced in the ethyl salicylate treated animals.

Preferred Dispersant

Polysorbate 80 would appear to be the preferred dispersant over ethanol or Tween 20™ (Trials #3, 4, 5 and 6). Tween 20™ appeared to produce an irritant effect that precluded Phase 4 anaesthesia in chinook salmon (Trials 3 and 4) while ethanol appeared to poorly disperse the salicylates and delayed the establishment of Phase 4 anaesthesia relative to Tween 20™ (Trial #5). Exposure of mullet to 80 mg/l Polysorbate 80 for 3 hours produced no noticeable effects on either behaviour or appearance (Trial #1).

Ethyl Salicylate/Iso-eugenol/Polysorbate 80 Mixtures

This mixture produced a very rapid onset of Phase 4 anaesthesia in mullet exposed to a combination of 50 mg/l ethyl salicylate and 20 mg/l iso-eugenol relative to exposure to 50 and 100 mg/l doses of ethyl salicylate (Trials #1 and 10). Phase 4 appeared to be unusually deep in this case. This is supported by the prolonged recovery period relative to the 50 mg/l ethyl salicylate treatment (Trial #10) and the 100 mg/l ethyl salicylate treatment (Trial #1). No muscle twitches or spasms were observed during this treatment while the apparent intensity of the alarm activity in Phases 1, 2 and 3 was reduced relative to the 50 and 100 mg/l treatments that used only ethyl salicylate. The combination of ethyl salicylate and iso-eugenol therefore exhibits synergistic properties.

Invertebrates

Trial #11 indicates that ethyl salicylate will anaesthetise invertebrate species such as molluscs. Anaesthetic effects are therefore likely to be found in a wide range of phylogenetically diverse aquatic species.

INDUSTRIAL APPLICATION

Thus, in accordance with the present invention there are provided methods and compositions for sedating/anaesthetising/euthanising aquatic organisms. Further, and most importantly, the active agents which are responsible for producing the sedating/anaesthetising/euthanising effect are additives which have very low or no toxicity and which are essentially non-irritating to the organism.

Those persons skilled in the art will therefore appreciate the advantages of the present invention as well as the many applications to which the methods and compositions of the present invention can be put. As a first example, the methods and compositions can be employed in the harvesting of aquatic organisms for ultimate human consumption. This is particularly so in the case of organisms such as fish which otherwise struggle violently to avoid capture, having a major impact on the post-mortem quality of the tissue. However, when sedated, anaesthetised or euthanised in accordance with the present methods this struggling is at least much reduced, if not eliminated. Further, any residual concentration of ethyl salicylate or methyl salicylate in the tissue of the organism following harvesting will be very low and will therefore not detract from the suitability of the flesh for hunan consumption.

Additionally, where the aquatic organism is a shellfish, sedation/anaesthetisation/ euthanisation of the shellfish greatly eases the extraction of the flesh from the shell.

A further application of the sedating, anaesthetising or euthanising methods and compositions is in the transportation of live aquatic organisms. This is once again particularly the case with fish which are to be transported live to overseas markets and where the natural undamaged appearance of the fish is critical to the market price obtained.

Still a further application of the invention is in the transport of aquatic organisms to a market where the organism is to be sold in a pre-rigor state. By "pre-rigor" it is meant a state in which the tissue of the organism remains alive for a prolonged period following administration of methyl salicylate and/or ethyl salicylate but in which the organism is no longer capable of control of its musculature and from which the organism will not recover. The organism is therefore in a state of "living death".

The advantage of transporting the organism in this pre-rigor state is that the organism need not be transported in its aquatic environment. Instead, the organism can be transported "dry", which represents a considerable reduction in expense over that associated with the transportation of live organisms in their aquatic environment.

Additionally, as the tissue of the organism remains alive until the organism has reached its market, the flesh remains "fresh" and able to command a market premium over flesh from organisms euthanised before transport.

Another application of the present invention is in the formulation of improved active compositions containing other food-grade aquatic sedative/anaesthetic compounds such as eugenol and iso-eugenol. A combination of ethyl salicylate and iso-eugenol has been found to be particularly advantageous and to have synergistic properties.

Other applications of the present methods and compositions will be readily apparent to the skilled worker in this art.

It will be appreciated that the above description is provided by way of example only and that the present invention is limited only by the lawful scope of the appended claims.

We claim:

1. A method of sedating, anaesthetising or euthanising an aquatic organism comprising the step of contacting said organism with a compound of the formula

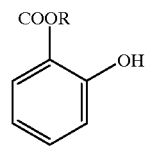

where R is methyl or ethyl.

2. A method of harvesting an aquatic organism while substantially retaining its pre-mortem flesh quality comprising the step of contacting said organism with a compound of the formula

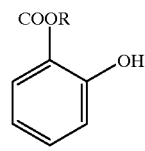

where R is methyl or ethyl.

3. A method of transporting an aquatic organism in a live or pre-rigor state comprising the steps of:

contacting the organism to be transported with a compound of the formula

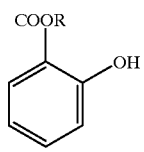

where R is methyl or ethyl in order to induce a sedated, anaesthetised or pre-rigor state in said organism; and transporting said organism while in said sedated, anaesthetised or pre-rigor state.

4. A method as claimed in claim 1 wherein said compound is methyl salicylate.

5. A method as claimed in claim 1 wherein the compound is ethyl salicylate.

6. A method as claimed in claim 1 wherein said compound is contacted with said organism in an admixture with one or more additional food-grade aquatic sedative, anaesthetic or euthanising agents.

7. A method as claimed in claim 6 wherein said admixture contains both methyl salicylate and ethyl salicylate.

8. A method as claimed in claim 6 wherein said admixture contains at least one of methyl and ethyl salicylate, and at least one of eugenol and iso-eugenol.

9. A method as claimed in claim 8 wherein said admixture contains ethyl salicylate and iso-eugenol.

10. A method as claimed in claim 1 wherein said compound or admixture is in solution.

11. A sedative, anesthetic or euthanising composition for use in sedating, anaesthetising or euthanising aquatic organisms which comprises, as sedative, anesthetic or euthanising agent, an effective amount of a compound of the formula

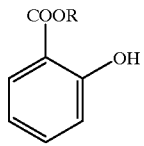

where R is methyl or ethyl, in admixture with an effective amount of a solvent or surfactant therefor.

12. A composition as claimed in claim 11 wherein said compound is methyl salicylate.

13. A composition as claimed in claim 11 wherein said compound is ethyl salicylate.

14. A composition as claimed in claim 11 containing a surfactant wherein said surfactant is Polysorbate 80.

15. A composition as claimed in claim 11 which includes both methyl salicylate and ethyl salicylate.

16. A composition as claimed in claim 11 which includes one or more additional food-grade aquatic sedative, anaesthetic or euthanising agents.

17. A composition as claimed in claim 16 wherein said additional agents are selected from eugenol and iso-eugenol.

18. A sedative, anesthetic or euthanising composition for use in sedating, anaesthetising or euthanising aquatic organisms which comprises, as sedative, anesthetic or euthanising agent, an effective amount of at least one compound of the formula

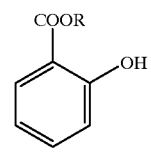

wherein R is methyl or ethyl, in admixture with an effective amount of at least one compound of the formula

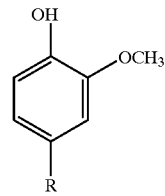

where R is $CHCHCH_3$ or $CH_2CHCH_2$.

19. A composition as claimed in claim 18 which comprises an admixture of methyl salicylate and one or both of eugenol and iso-eugenol.

20. A composition as claimed in claim 18 which comprises an admixture of ethyl salicylate and one or both of eugenol and iso-eugenol.

21. A composition as claimed in claim 18 which comprises an admixture of methyl salicylate, ethyl salicylate and one or both of eugenol and iso-eugenol.

22. A composition as claimed in claim 18 which comprises ethyl salicylate and iso-eugenol.

23. A composition as claimed in claim 18 further including a surfactant.

24. A composition as claimed in claim 23 wherein the surfactant is Polysorbate 80.

* * * * *